United States Patent [19]
Orth

[11] Patent Number: 5,800,521
[45] Date of Patent: Sep. 1, 1998

[54] PROSTHETIC GRAFT AND METHOD FOR ANEURYSM REPAIR

[75] Inventor: Geoffrey A. Orth, El Granada, Calif.

[73] Assignee: Endotex Interventional Systems, Inc., Menlo Park, Calif.

[21] Appl. No.: 749,082

[22] Filed: Nov. 14, 1996

Related U.S. Application Data

[63] Continuation of Ser. No. 472,700, Jun. 6, 1995, abandoned, which is a continuation-in-part of Ser. No. 336,875, Nov. 9, 1994, abandoned.

[51] Int. Cl.$^6$ ............................................. A61F 2/06
[52] U.S. Cl. ..................... 623/1; 606/194; 606/195; 606/198; 623/11; 623/12
[58] Field of Search ........................ 623/1, 11, 12, 623/66; 606/108, 153, 155, 156, 158, 191–195, 198, 200; 128/898

[56] References Cited

U.S. PATENT DOCUMENTS

| | | |
|---|---|---|
| 3,657,744 | 4/1972 | Ersek . |
| 4,562,596 | 1/1986 | Kornberg . |
| 4,580,568 | 4/1986 | Gianturco . |
| 4,617,932 | 10/1986 | Kornberg . |
| 4,733,665 | 3/1988 | Palmaz . |
| 4,787,899 | 11/1988 | Lazarus . |
| 4,830,003 | 5/1989 | Wolff et al. . |
| 4,872,874 | 10/1989 | Taheri .......................... 623/1 |
| 4,994,071 | 2/1991 | MacGregor . |
| 5,035,706 | 7/1991 | Giantureo et al. . |
| 5,078,726 | 1/1992 | Kreamer . |
| 5,104,399 | 4/1992 | Lazarus . |
| 5,104,404 | 4/1992 | Wolff . |
| 5,135,536 | 8/1992 | Hillstead . |
| 5,219,355 | 6/1993 | Parodi et al. . |
| 5,275,622 | 1/1994 | Lazarus et al. . |
| 5,282,824 | 2/1994 | Gianturco . |
| 5,282,846 | 2/1994 | Schmitt . |
| 5,282,847 | 2/1994 | Trescony et al. . |
| 5,282,848 | 2/1994 | Schmitt . |
| 5,316,023 | 5/1994 | Palmaz et al. . |
| 5,456,713 | 10/1995 | Chuter ........................... 606/195 |
| B1 4,733,665 | 1/1994 | Palmaz . |

FOREIGN PATENT DOCUMENTS

| | | |
|---|---|---|
| 91304988.8 | 6/1991 | European Pat. Off. . |
| 91308991.8 | 10/1991 | European Pat. Off. . |
| 91309197.1 | 10/1991 | European Pat. Off. . |
| 92309777.8 | 10/1992 | European Pat. Off. . |

*Primary Examiner*—Robert A. Clarke
*Assistant Examiner*—Francis K. Cuddihy
*Attorney, Agent, or Firm*—Fish & Neave; Nicola A. Pisano

[57] ABSTRACT

This invention provides a method and graft system for aneurysm repair comprising a prosthetic graft with means to draw a distal extremity of the graft over a portion of an expandable anchoring member. Prior to deployment, the graft and the anchoring member do not overlap to reduce the outer diameter of the delivery system. Preferably, the drawing means comprises pull strands connected to the distal extremity of the graft so that the distal extremity of the graft may be pulled over a proximal portion of the anchoring member. Subsequent expansion of the anchoring member seals the overlapped graft against the vessel wall to minimize blood flow-by and secures the graft in the vessel. Securing means may be advanced up each pull strand to abut the anchoring member and further secure the graft to the anchoring member.

The graft may also comprise means to guide a second expandable anchoring member to the proximal end of the graft. Preferably, the guiding means comprise guide strands connected to a proximal extremity of the graft. The anchoring member can then be advanced up the guide strands until the graft overlaps the second anchoring member. Expansion of the second anchoring member secures the proximal end of the graft.

22 Claims, 2 Drawing Sheets

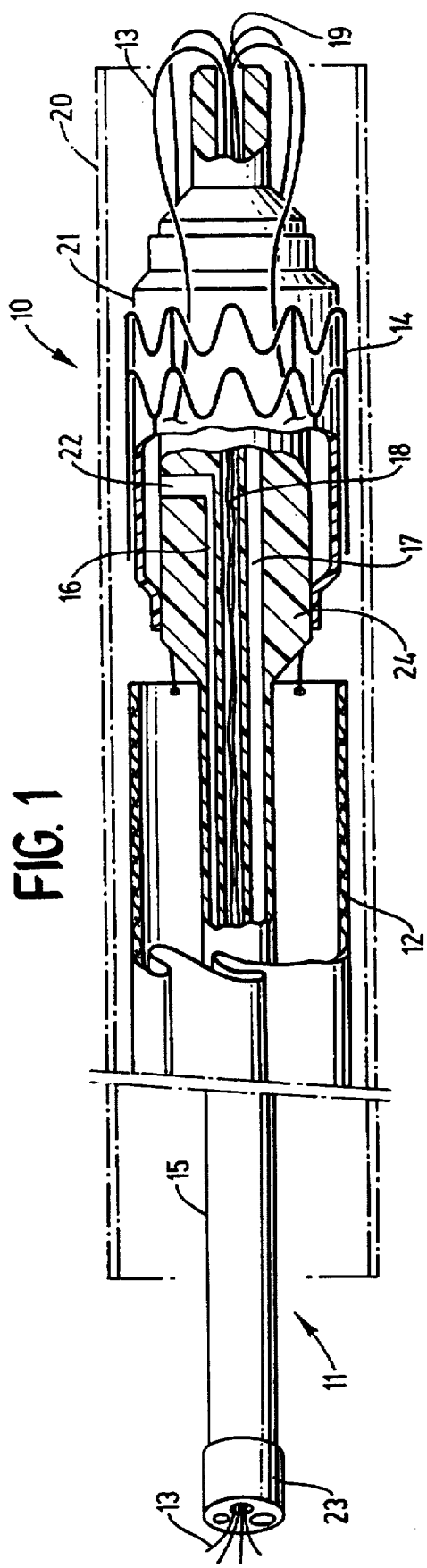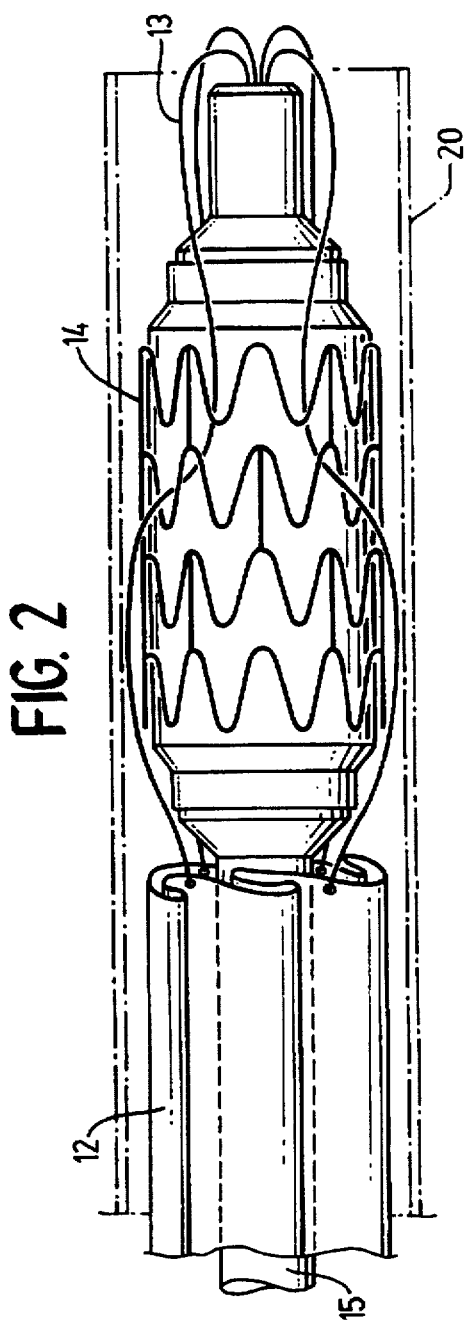

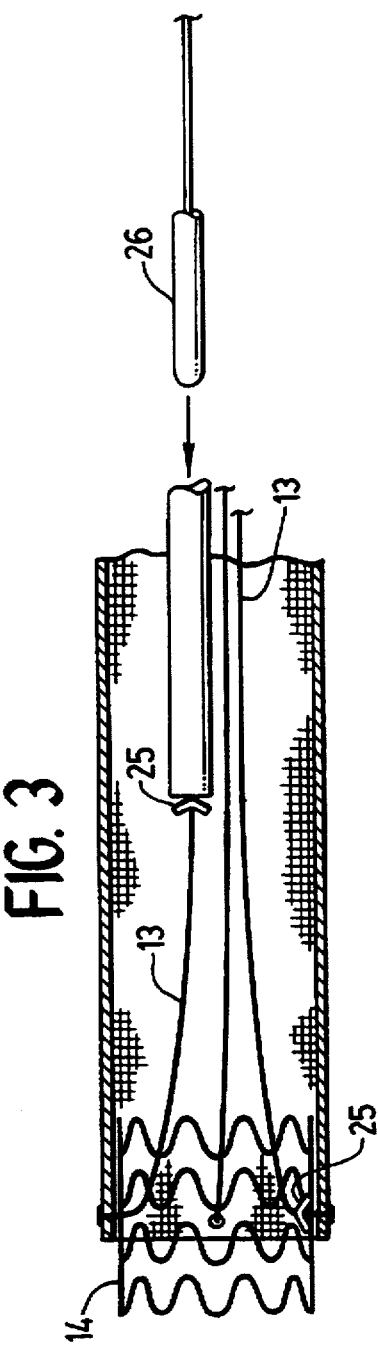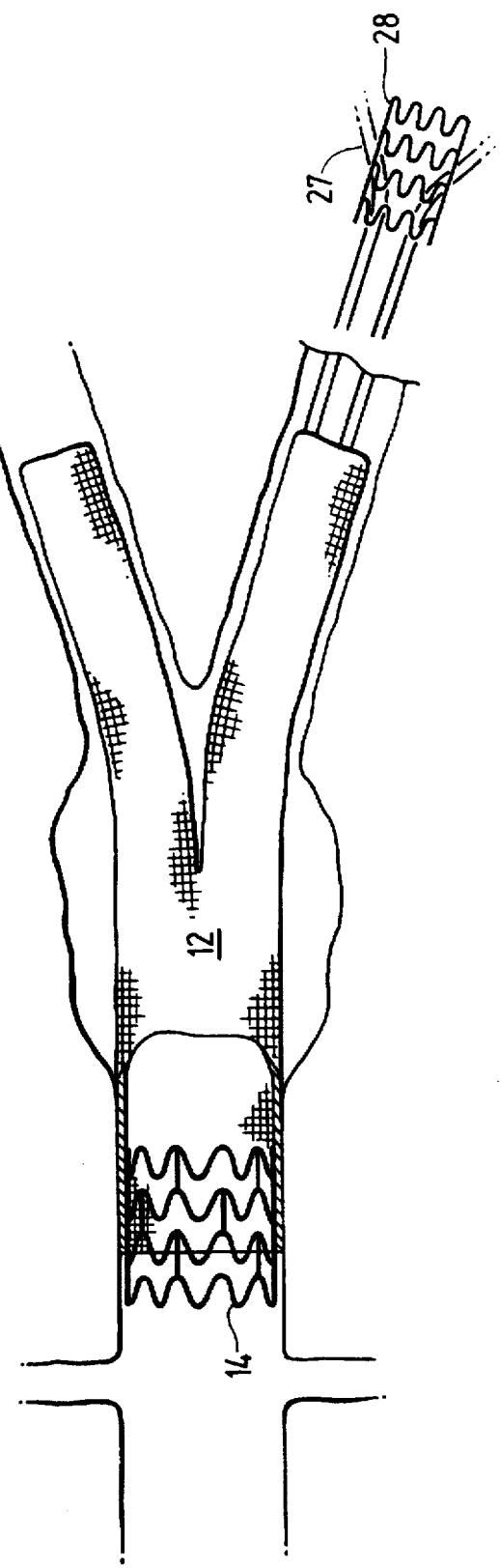

PROSTHETIC GRAFT AND METHOD FOR ANEURYSM REPAIR

This is a continuation of application U.S. Ser. No. 08/472,700, filed Jun. 6, 1995, now abandoned, entitled PROSTHETIC GRAFT AND METHOD FOR ANEURYSM REPAIR which is a continuation-in-part of U.S. application Ser. No. 08/336,875, filed Nov. 9, 1994, now abandoned, entitled DELIVERY CATHETER AND GRAFT FOR ANEURYSM REPAIR.

BACKGROUND

This invention relates to the delivery and placement of vascular grafts, and in particular, to a method and system for the repair of abdominal aortic aneurysms.

An aneurysm is a sac resulting from abnormal dilation of the artery wall and is often associated with arteriosclerotic disease. Unless treated, an aneurysm can rupture, leading to severe and often fatal hemorrhaging. Treating an aortic aneurysm generally involves transplanting a prosthetic graft to bridge the affected section of the aorta. Surgical implantation of the graft is possible but this treatment causes considerable trauma, results in high mortality and morbidity and, even when completely successful, requires a lengthy recuperation period. Due to the difficulty of the operation, direct surgical replacement is even less attractive when it must be performed on an emergency basis after the aneurysm has ruptured.

A less invasive alternative involves the use of a catheter to effect intraluminal delivery of a graft. Prior art graft delivery systems, such as disclosed in EP 0 461 791 A1 (Barone et al.), employ a graft with expandable portions that anchor the graft in the aorta. Often, the systems use an inflatable balloon on the delivery catheter to expand the anchoring portion of the graft as disclosed In U.S. Pat. No. 5,275,622 (Lazarus et al.) which is hereby incorporated in its entirety by reference thereto.. This latter example requires the use of a bulky capsule to store the graft and a complicated pushrod system to deploy the graft.

Although the referenced prior art systems and others employ many different stent and graft configurations, none are completely satisfactory. The principle limitation of the prior art systems is their size. They typically require a delivery catheter having a diameter of approximately 24–28 French (8 to 9.3 mm). Although it is desirable to introduce grafts through the femoral artery, its inner diameter is only about 4 to 6 mm. Thus, the size of the prior art devices restricts them to introduction through upper femoral sites, where access may be difficult. Accordingly, there is a need for a graft system capable of introduction through a smaller opening while maintaining the ability to reliably and securely deploy the graft.

The success of a percutaneous vessel repair depends in large part on getting the graft to the location of the vasculature in need of repair and deploying the graft effectively. Another difficulty associated with prior art graft deployment systems is blood flow-by which occurs when blood can pass between the graft and the patient's vessel, bypassing the graft. There is a need for a graft system which minimizes or prevents flow-by.

SUMMARY OF THE INVENTION

This Invention provides a method and graft system for aneurysm repair which generally comprises a prosthetic graft with means to draw a distal extremity of the graft over a portion of an expandable anchoring member. For deployment, the graft and the anchoring member are radially compressed and positioned adjacent one another coaxially on a delivery catheter with essentially no overlap between the distal end of the graft and the proximal end of the anchoring member. The drawing means is connected to the distal extremity of the graft so that when tension is applied to the graft by the drawing means, the distal extremity of the graft is caused to overlap a proximal portion of the anchoring member. Subsequent expansion of the anchoring member seals the overlapped graft against the vessel wall to minimize blood flow-by and secures the graft in the vessel. Since the graft and anchoring member do not overlap when loaded on the catheter prior to deployment, the system maintains an overall low profile.

In a preferred embodiment, the drawing means comprises at least one and preferably four pull strands attached to the distal end of the graft. The pull strands extend outside the distal end of the catheter, are threaded through an opening at the distal end of the delivery catheter and extend through a lumen in the catheter to the proximal end. After the graft is properly positioned within a patient's vasculature, tension is applied to the pull strands to cause the graft to slide distally along the catheter until the distal end of the graft extends over the proximal end of the anchoring member. Subsequent expansion of the anchoring member expands the graft, anchors it against the vessel wall and seals the graft against the vessel wall to minimize blood flow-by. Securing means may be advanced up the pull strand to abut the anchoring member and further secure the graft to the anchoring member.

The graft may also comprise means to guide a second expandable anchoring member to the proximal end of the graft. The guiding means are connected to a proximal extremity of the graft. In one embodiment, the guiding means comprises at least one and preferably four guide strands. After the distal end of the graft is anchored within the patient's vasculature, the guide strands are laced through the second anchoring member. The anchoring member can then be advanced up the guide strands until it is at least partially overlapped by the proximal end of the graft. The graft overlaps the second anchoring member and expansion of the anchoring member secures the proximal end of the graft. Preferably, securing means secure the proximal end of the graft to the second anchoring member as described above regarding the drawing means.

BRIEF DESCRIPTION OF THE DRAWINGS

FIG. 1 is a sectional elevation of a delivery catheter and graft system embodying features of this invention.

FIG. 2 is an elevational view of a distal portion of a delivery catheter and graft system of the invention comprising a self-expanding stent.

FIG. 3 shows an embodiment of the invention comprising pull strand securing means.

FIG. 4 illustrates an embodiment of the invention comprising guiding means and downstream graft anchoring.

DETAILED DESCRIPTION OF THE INVENTION

FIG. 1 is a elevational view, in section, illustrating a catheter system 10 embodying features of the invention which generally comprises a catheter 11 with an aortic graft 12 having drawing means, a plurality of pull strands 13, attached to the distal end and an expandable anchoring member, stent 14, loaded for delivery. The catheter 11 comprises a flexible catheter shaft 15 with proximal and distal ends, an inflation lumen 16, a guidewire lumen 17 and a pull strands lumen 18. Pull strands 13 extend from graft 12, enter the pull strands lumen 18 through opening 19 at the distal end of catheter 11 and exit from the proximal end of catheter 11. Preferably, pull strands 13 may be laced through stent 14 at a point corresponding to the amount of overlap desired. In a preferred embodiment, graft 12 overlaps about half the length of stent 14 prior to expansion. A thin-walled retractable sheath 20 is slidably disposed over the catheter 11 and configured so that it covers the stent 14 and graft 12 during introduction and placement of the catheter system 10 and may be withdrawn once they are in an appropriate position within the patient. In the embodiment of FIG. 1, the catheter 11 includes an inflatable balloon 21 in fluid communication with the inflation lumen 16 through inflation passage 22 which is configured to expand stent 14. The proximal end of catheter shaft 15 can have a cap 23 bonded to the end to provide access to inflation lumen 16, guidewire lumen 17 and pull strands lumen 18. The configuration of cap 23 allows it to mate in a conventional manner with a multi-arm adaptor (not shown) that supplies inflation fluid and allows guidewire control and manipulation of the pull strands. Cap 23 Is preferably formed from metal, although other materials such as plastics are suitable. The diameter of cap 23 allows the compressed graft 12 and stent 15 to be threaded over the proximal end of catheter shaft 14. In a preferred embodiment, catheter shaft 15 has an increased diameter delivery base 24 under balloon 21. The delivery base 24 provides support for the expansion of stent 14 while allowing the remainder of the catheter shaft 15 to have a relatively small diameter. Further details regarding the design of suitable catheters as well as graft and stent materials may be found in the application Ser. No. 08/336, 875, filed Nov. 9, 1994, which is hereby incorporated in its entirety by reference.

Preferably, the stent 14 is a Bronco® stent, available from Advanced Cardiovascular Systems, Inc. of Santa Clara, Calif. Alternatively, stent 14 may be self-expanding as shown in FIG. 2. For example, stent 14 may be constructed from shape-memory materials causing it to revert to its expanded shape at body temperatures. In such embodiments, thin-walled sheath 20 would restrain stent 14 until properly positioned. Other suitable means for expanding the stent may be used.

The effective wall thickness of stent 14 does not change between the pre-expanded and expanded states. On the other hand, the graft 12 bunches when compressed to conform to the catheter shaft 15 and forms overlaps and pleats, effectively increasing Its wall thickness. Stent 14 and graft 12 are coaxially threaded over the catheter 11; the relatively thick compressed graft 12 is positioned solely over the relatively small diameter catheter shaft 15 while the stent 14 receives the Increased support for expansion provided by larger diameter delivery base 24. The lack of overlap between the graft 12 and the stent 14 when loaded for deployment on catheter shaft 15 saves approximately 1–3 mm from the diameter of system 10 over conventional systems. Accordingly, the delivery catheters of this invention have an insertion diameter of less than 7 mm and preferably about 6 mm. This allows system 10 to present a small outer diameter to facilitate introduction into the body, preferably through the femoral artery.

In embodiments where pull strands 13 are laced through stent 14, securing means 25 may be employed to further anchor the graft 12 as shown in FIG. 3. The securing means 25 thread over pull strands 13 and are configured so that they will not pass through the framework of stent 14. In one embodiment, securing means 25 comprise one-way frictional sliding washers. Once graft 12 and stent 14 are deployed and catheter 11 removed, a simple catheter 26 is used to push securing means 25 up pull strands 13 until they are tightly seated against stent 14. This secures pull strands 13 to stent 14 and further anchors the graft 12.

FIG. 4 illustrates an embodiment of the invention which comprises guiding means, guide strands 27, attached to the proximal end of graft 12. Guide strands 27 are similar in configuration to pull strands 13. In use, the graft's distal end (or ends in the case of a bifurcated graft) 12 may be anchored by lacing guide strands 27 through a second anchoring member, stent 28, and advancing the stent 28 up the guide strands until the proximal end of graft 12 at least partially overlaps stent 28. Once positioned, the anchoring member 28 is expanded to secure the proximal end of graft 12 and maintain the graft's patency. Securing means 25 may be used to further anchor the graft as described above. In some embodiments, the guide strands 27 are attached to the interior of graft 12 at a point inset from the proximal end to allow that proximal portion of graft 12 to overlap a distal portion of stent 28 such that expansion of stent 28 will sandwich the proximal end of the graft against the patient's vessel wall.

In general, anchoring members may be formed from any suitable material, including tantalum, stainless steel, other metals and polymers and when employing a self-expanding anchoring member, shape-memory metals such as NiTi alloys. The anchoring member may also be coated with a polymer or seeded with endothelial cells to further inhibit thrombosis. Generally, the anchoring member is formed in its pre-expanded state. Once it is positioned with the graft over the catheter shaft 15, the anchoring member may be crimped down to a slightly smaller inner diameter onto the means for expanding the anchoring member to secure the assembly during introduction and to further reduce the delivery diameter. Anchoring member configurations are suitable so long as they are self supporting within the aortic passageway and provide suitable means for anchoring the graft.

The grafts of this invention are intact tubes, preferably constructed of a synthetic yarn, monofilament or multifilament, formed from materials such as polyesters (including Dacron®), polytetrafluoroethylene (PTFE), polyurethane or nylon. Dacron® in particular, a multifilament composed of polyethylene terephthalate (PET), has been shown to be suitable and may promote formation of intima. The synthetic material may be woven or knit. The woven grafts are generally stronger and less porous while knit grafts are softer and more porous. Additionally, the surface of the synthetic material may be texturized and woven or knit to form a velour surface which generally facilitates growth of tissue from the surrounding lumen through the velour loops to help secure the graft. If desirable, the graft may be bifurcated.

The catheter 11 may be formed from any suitably flexible material, such as pseudoelastic metals (e.g. NiTi alloys) and a wide range of conventional polymers. Preferably, the catheter 11 is formed from an extrudable polymer such as polyethylene (PE).

The inflatable balloon 21 may be a relatively inelastic inflatable balloon to provide the degree of expansion control and durability necessary to effectively expand and anchor the anchoring member. The balloon may be formed from any suitable material such as PE, polyethylene terephthalate (PET) or nylon or other polyamide.

Pull strands 13 and guide strands 27 may comprise any suitable material having sufficient flexibility to easily thread through the anchoring means and the catheter while having sufficient strength to pull the graft over the stent. Suitable materials include plastics and metals. In some embodiments, pull strands 13 and guide strands 27 may comprise integral parts of the graft 12. It may be desirable to form all or a portion of pull strands 13 and guide strands 27 from a bioabsorbable material. It is preferable to provide the graft 12 with four pull strands 13 and four guiding strands 27, each radially spaced around the respective end of the graft.

The use of the catheter system 10 generally follows conventional procedures. In particular, a guidewire (not shown) is backloaded into guidewire receiving lumen 17 of the catheter 11 with sheath 20 extending over the compressed and loaded graft 12 and stent 14, as shown in phantom. The catheter system 11 and guidewire are percutaneously introduced by means of conventional cut down techniques in the patient's arterial system, generally through the femoral artery. The guidewire is advanced out delivery catheter 11 and up the aorta via fluoroscopic imaging until it crosses the aneurysm. Then the catheter 11 is advanced over the guidewire until the stent 14 is positioned within a healthy region of the aorta upstream from the aneurysm. The sheath 20 is retracted to expose the stent 14 and the graft 12. Pull strands 13 are pulled to draw the distal end of the graft a desired amount over the proximal end of the stent 14, preferably half the length of the stent. Then, balloon 21 is inflated to expand stent 14 to sandwich the distal end of graft 12 between the stent 14 and the aortic wall, thus anchoring it. The balloon 21 is deflated and the catheter 11 is removed, leaving the expanded anchoring member and graft in place. To further secure the graft, securing means 25 may be advanced up pull strands 13 until they abut the stent 14. Once securing means 25, if any, are positioned, all excess of the pull strands 13 may be cut.

Once deployed, the proximal end or ends of graft 12 may be anchored by advancing another anchoring member 28 along guide strands 27. Securing means 25 may also be employed to further anchor the proximal end of graft 12 to anchoring member 28.

While the invention has been described primarily with respect to a system comprising the catheter loaded with an anchoring member and graft, it includes the graft with drawing means alone, kits which comprise unassembled catheters, anchoring members and grafts, and methods of use. It should be recognized that various modifications and improvements can be made to the invention without departing from the scope thereof.

What is claimed is:

1. A graft delivery system comprising:
   a) an elongated catheter with proximal and distal ends and a means for expanding an expandable anchoring member on a distal portion of the catheter;
   b) an expandable anchoring member with proximal and distal ends mounted on the means for expanding;
   c) an aortic graft in a radially compressed state with proximal and distal ends and mounted on the catheter proximally adjacent to, and non-overlapping the proximal end of, the anchoring member; and
   d) drawing means secured to the distal end of the graft and configured to pull the distal end of the graft to overlap the proximal end of the anchoring member.

2. The graft delivery system of claim 1 wherein the catheter further comprises a lumen with an opening at the distal end and extending to the proximal end and the drawing means comprises at least one pull strand extending from the distal end of the graft through the opening at the distal end of the catheter to the proximal end of the catheter.

3. The graft delivery system of claim 2 wherein the pull strand is laced through the anchoring member.

4. The graft delivery system of claim 1 wherein the means for expanding an anchoring member comprises an inflatable member.

5. The graft delivery system of claim 4 including an inflation lumen extending through the catheter in fluid communication with the interior of the inflatable member.

6. The graft delivery system of claim 1 wherein the system has an outer diameter of less than about 7 mm.

7. The graft delivery system of claim 1 wherein the anchoring member comprises a stent.

8. The graft delivery system of claim 1 wherein the graft further comprises guiding means extending from the proximal end of the graft.

9. The graft delivery system of claim 8 wherein the guiding means comprise at least one guiding strand.

10. A graft delivery system comprising:
    a) an elongated catheter with proximal and distal ends;
    b) a self-expanding anchoring member with proximal and distal ends mounted on a distal portion of the catheter;
    c) an aortic graft in a radially compressed state with proximal and distal ends and mounted on the catheter proximally adjacent to, and non-overlapping the proximal end of, the anchoring member; and
    d) drawing means secured to the distal end of the graft and configured to pull the distal end of the graft to overlap the proximal end of the anchoring member.

11. The graft delivery system of claim 10 wherein the catheter further comprises a lumen with an opening at the distal end and extending to the proximal end and the drawing means comprise pull strands extending from the distal end of the graft through the opening at the distal end of the catheter to the proximal end of the catheter.

12. The graft delivery system of claim 11 wherein the pull strands are laced through the anchoring member.

13. The graft delivery system of claim 10 wherein the self-expanding anchoring member is formed from shape-memory material.

14. The graft delivery system of claim 13 wherein the anchoring member is formed from a NiTi alloy.

15. The graft delivery system of claim 10 wherein the graft further comprises guiding means extending from the proximal end of the graft.

16. The graft delivery system of claim 15 wherein the guiding means comprise at least one guiding strand.

17. A method for repairing a portion of a patient's vasculature comprising the steps of:
    a) providing a catheter assembly having:
       1) an elongated catheter with proximal and distal ends and a means for expanding an expandable anchoring member on a distal portion of the catheter,
       2) an expandable anchoring member with proximal and distal ends mounted on the expanding means,
       3) an aortic graft in a radially compressed state with proximal and distal ends and mounted on the catheter proximally adjacent to, and non-overlapping the proximal end of, the anchoring member, and
       4) drawing means secured to the distal end of the graft and configured to pull the distal end of the graft to overlap the proximal end of the anchoring member; and
    b) advancing the catheter assembly with the graft to the desired location in the patient's vasculature;

c) operating the drawing means to pull the distal end of the graft to overlap the proximal end of the anchoring member; and d) expanding the anchoring member to expand and anchor the graft within the patient's vasculature.

18. The method for repairing a portion of a patient's vasculature of claim 17 further comprising the step of attaching securing means on drawing means abutting the anchoring means to anchor the graft.

19. The method for repairing a portion of a patient's vasculature of claim 17 wherein the graft further comprises guiding means and further comprising the steps of:

a) lacing the guiding means through a second anchoring member;

b) advancing the second anchoring member along the guiding means through the patient's vasculature until the second anchoring member is at least adjacent to the proximal end of the graft; and c) expanding the second anchoring member to anchor the proximal end of the graft.

20. A method for repairing a portion of a patient's vasculature comprising the steps of:

a) providing a catheter assembly having:
 1) an elongated catheter with proximal and distal ends,
 2) a self-expanding anchoring member with proximal and distal ends mounted on a distal portion of the catheter,
 3) an aortic graft in a radially compressed state with proximal and distal ends and mounted on the catheter proximally adjacent to, and non-overlapping the proximal end of, the anchoring member, and
 4) drawing means secured to the distal end of the graft and configured to pull the distal end of the graft to overlap the proximal end of the anchoring member; and b) advancing the catheter assembly with the graft to the desired location in the patient's vasculature;

c) operating the drawing means to pull the distal end of the graft to overlap the proximal end of the anchoring member; and d) allowing the self-expanding anchoring member to expand and anchor the graft within the patient's vasculature.

21. The method for repairing a portion of a patient's vasculature of claim 20 further comprising the step of attaching securing means on drawing means abutting the anchoring means to anchor the graft.

22. The method for repairing a portion of a patient's vasculature of claim 20 wherein the graft further comprises guiding means and further comprising the steps of:

a) lacing the guiding means through a second anchoring member;

b) advancing the second anchoring member along the guiding means through the patient's vasculature until it is at least adjacent to the proximal end of the graft; and c) expanding the second anchoring member to anchor the proximal end of the graft.

* * * * *